A. RALPH.

Packing-Machine.

No. 6,457. Reissued May 25, 1875.

WITNESSES

Chas. F. Vaw Horn

Geo. C. Holmes

INVENTOR

Alexander Ralph by Francis D. Pastorius

Atty

BEST AVAILABLE COPY

UNITED STATES PATENT OFFICE.

ALEXANDER RALPH, OF PHILADELPHIA, PENNSYLVANIA.

IMPROVEMENT IN PACKING-MACHINES.

Specification forming part of Letters Patent No. 142,851, dated September 9, 1873; reissue No. 6,457, dated May 25, 1875; application filed April 8, 1875.

*To all whom it may concern:*

Be it known that I, ALEXANDER RALPH, of Philadelphia, Pennsylvania, have invented a Packing-Machine, of which the following is a specification:

The invention relates to a machine for packing bottles and packages with flour, snuff, spices, and other material. It is so fully and accurately described hereafter that a preliminary description is not deemed necessary.

Figure 1:
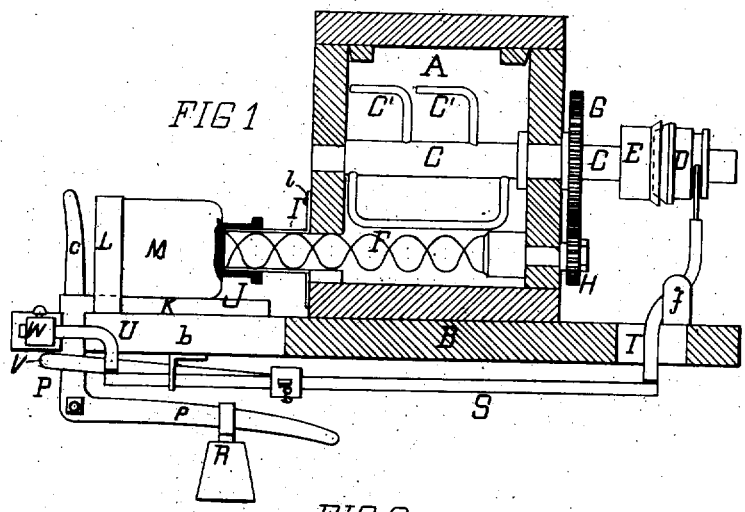
Figure 2:
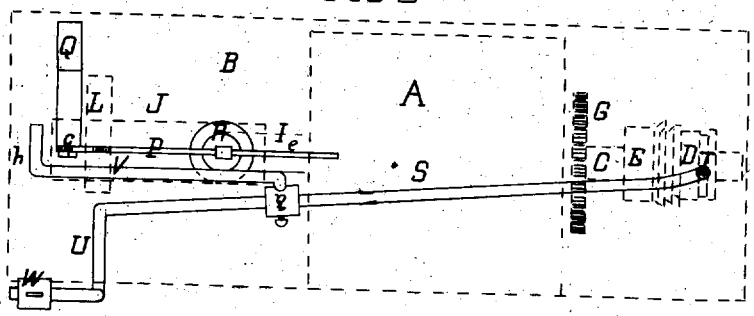
Figure 3:
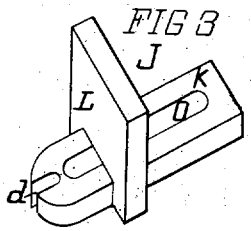
Figure 4:
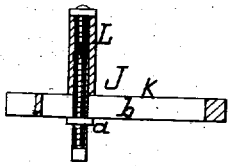
Figure 5:
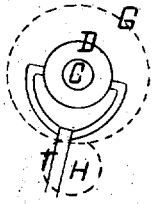
Figure 6:
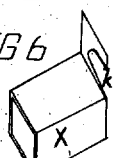
Figure 7:
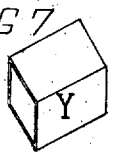

Figure 1 is a side elevation, partly sectioned, of a machine which embodies my invention. Fig. 2 is a plan view of the operative parts situated beneath the top or stand of the machine; the standand the parts above it are shown in dotted lines. Fig. 3 is a perspective view of the bottle and package holder and carrier. Fig. 4 is a longitudinal vertical section of the bottle and package holder and carrier. Fig. 5 is an end view of the friction cone-pulleys and shifting-clutch. Figs. 6, 7 are perspective views of the devices employed when filling packages.

A is a hopper on the top B of the machine. C is a horizontal shaft placed lengthwise with the machine, partly within and partly without the hopper. Its outer end carries the friction cone-pulleys D E for transmitting motion. The length within the hopper has one or more whippers or agitators, C′, fixed to it. F is a feed and packing screw in the hopper below, and parallel with the shaft C, with which it is connected, and from which it receives motion by means of the spur-gear and pinion G H, respectively, on the said shafts. I is a feed-spout extending horizontally from the front of the hopper. It contains the prolongation of the screw F, and serves for a support, guide, and feeder for the bottles and packages to be filled. J is a bottle and package holder and carrier. It is constructed substantially as shown at Figs. 3, 4. The bed or base K rests on the top B of the stand, in front of and in line with the spout I. Its butting-rest L, against which the base of the bottle or package M bears when filling, is arranged vertically and transversely to the bed. A screw-bolt, N, which is inserted either in its bottom edge, or extended its length, with a nut at top and bottom, takes through a longitudinal slot, O, in the bed, and enables the butting-block to be adjusted at any required part of the bed K to suit the holder and carrier to the varying lengths of the bottles and packages. The rectilinear motion of the follower is preserved by the bolt head or nut *a* in a corresponding groove, *b*, in the top B. P, Figs. 1, 2, is a compressing-lever, which turns on a fulcrum, Q, depending from the under side of the top B. Its vertical leg *c* extends a suitable distance above the stand, and takes into a notch or slot, *d*, in the continuation of the bed K of the carrier J. Its horizontal leg *e* extends beneath the table. It carries an adjustable weight, R, for giving the necessary force to the leg *c*. S is a shifting-bar placed lengthwise beneath the top. One end of it joints with the friction-clutch lever T, which turns on the fulcrum *f*, and engages with the friction-pulley D. Its outer end connects with the bent weighted lever U. V is a trip-rod attached to an adjustable collar, *g*, on the shifting-bar S. Its bent or turned end *h* takes directly behind the vertical leg *c* of the compression-lever P. The cones or friction-pulleys D E are as follows: The cone D turns with the shaft C, and has a sliding motion on it by means of a feather. Its conical or tapering end (dotted lines, Fig. 1) takes into a similar cone-shaped recess in the friction-pulley E, which turns loosely on the shaft, and is belted with the driving-pulley of the machine. When the pulleys are in contact, as shown, the machine can be run, but when apart it will be quiescent. The degree of compression or closeness of packing of the material in the bottle or package is governed by the weight of material to be packed in the said bottle or package. When this is determined, the weight R is adjusted on the leg *e* of the lever P, to exert that degree of resistance to the retreat of the bottle or package to attain the desired compression or closeness of packing. The collar *g* is also set at a point of the shifting-bar S to permit the leg *c* to strike the bent or turned end *h* at the proper moment for stopping the machine. The first few bottles filled are usually trial ones, to enable the operative parts to act in conjunction, so that the machine may perform its work without interruption. After the bottle or package M on the holder and carrier J has been passed a suitable distance over the spout I, and the snuff, spice, or other material filled in the hopper A, the machine is started. The agitators C′ thoroughly stir and keep the material fed to the screw F, which carries and packs it in the bottle or package. During the process of packing, the bottle gradually recedes until it is filled, when the leg *c* of the lever P contacts with the bent end *h* of the trip-rod V, and throws back the shifting-bar S, which causes the clutch-lever T to separate the friction-cones D E, and thus stop the machine. After the bottle has been taken from the carrier J, and all resistance removed, the weight W of the bent lever U acts by turning and reversing the position of the shifting-bar S, which causes the clutch-lever T to throw the friction-pulleys again in contact.

When packages are to be filled the process is the same, excepting that forms are used. The first form X, Fig. 6, has the paper or other wrapping material formed over it. The form-retainer Y, Fig. 7, is then slipped over all, and the whole passed over the spout, and secured from turning by the slot *k* taking over a button, *l*, at the front of the machine.

When the machine is in operation, the lid of the hopper must be kept in place; otherwise the agitators will throw the material from it. The bottom of the hopper, when shelving or inclined, causes the screw to run, as it were, in a trough.

I claim as my invention—

1. In a packing-machine, the combination of a hopper, A, a feed-screw, F, a feed-spout, I, and a yielding package-carrier, J, as shown and described.

2. The shaft C, in combination with the cone friction-pulleys D E, for the purpose shown and described.

3. The shaft C, pulleys D E, gear-wheels G H, and the screw F, as shown and described.

4. The combination of the hopper A, shaft C, cone-pulleys D E, agitators C′, screw F, and the gear-wheels G H, as and for the purpose shown and described.

5. The follower J, when constructed as shown and described.

6. The screw F, carrier J, and the weighted lever P, as shown.

7. The shifting-bar S, in combination with the clutch-lever T and the trip-rod V, as shown.

8. The shifting-bar S, in combination with the clutch-lever T, trip-rod V, weighted lever P, and the friction-cones D E, as shown.

9. The shifting-bar S, in combination with the clutch-lever T, friction-cones D E, and the weighted lever U, as shown.

10. The former X, in combination with the form-retainer Y, as shown.

In testimony whereof I hereunto sign my name in presence of two subscribing witnesses.

ALEXANDER RALPH.

Witnesses:
JAMES HAGAN,
FRANCIS D. PASTORIUS.